United States Patent [19]
Sobel

[11] Patent Number: 5,491,954
[45] Date of Patent: Feb. 20, 1996

[54] SUTURE WINDER MACHINE

[75] Inventor: Martin Sobel, Flemington, N.J.

[73] Assignee: Ethicon, Inc., Somerville, N.J.

[21] Appl. No.: 181,591

[22] Filed: Jan. 13, 1994

[51] Int. Cl.[6] .................................................. B65B 63/04
[52] U.S. Cl. ................ 53/116; 53/118; 53/147; 53/247; 53/255; 53/281
[58] Field of Search ............................ 206/63.3; 53/116, 53/118, 147, 155, 156, 235, 237, 238, 247, 255, 267, 268, 281, 544, 429, 430, 443, 467, 445, 446, 473, 474, 475

[56] References Cited

U.S. PATENT DOCUMENTS

| | | | |
|---|---|---|---|
| 3,167,895 | 2/1965 | Egler et al. | 53/473 |
| 3,490,192 | 1/1970 | Regan | 53/473 X |
| 3,618,282 | 11/1971 | Hagel et al. | 53/116 X |
| 3,811,244 | 5/1974 | Killen et al. | 53/116 |
| 3,816,889 | 6/1974 | Crotti | 53/116 |
| 4,255,917 | 3/1981 | Stone | 53/116 X |
| 4,424,898 | 1/1984 | Thyen et al. | |
| 4,922,904 | 5/1990 | Uetake et al. | |
| 5,165,217 | 11/1992 | Sobel et al. | 53/430 |
| 5,179,818 | 1/1993 | Kalinski et al. | 53/430 |
| 5,228,565 | 7/1993 | Sinn | 53/473 X |

Primary Examiner—John Sipos
Assistant Examiner—Daniel Moon
Attorney, Agent, or Firm—Scully, Scott, Murphy & Presser

[57] ABSTRACT

A suture winder machine and, more particularly, a semi-automated suture winding station of the machine adapted to facilitate the high-speed winding of multiple sutures, which are each attached to needles, into a peripheral channel of a tray utilized for packaging the needles and attached sutures. A substantially flat suture tray loaded with multiple needles and sutures extending therefrom is mounted on a rotatable platform incorporating registration structure for ensuring the appropriate mounting and positioning of the suture tray thereon, and with the winding machine containing operative structure adapted to rotate the suture tray about an axis perpendicular to the planar surface thereof so as to enable the extending multiple sutures to be bundled and wound for depositing in a channel formed along the periphery of the suture tray. The winding station of the machine includes cam-controlled stylus and suture guide structure; with the stylus engaging successive resilient fingers on the tray covering the channel during rotation of the tray on the platform on which the package is supported for rotation, so as to in cooperation with the suture guide, cause the sutures to be continually introduced into the channel beneath the raised fingers. Also disclosed is a cover-applying apparatus for attaching covers to the trays and concurrently forming product-labeling structure fastened to the trays.

15 Claims, 6 Drawing Sheets

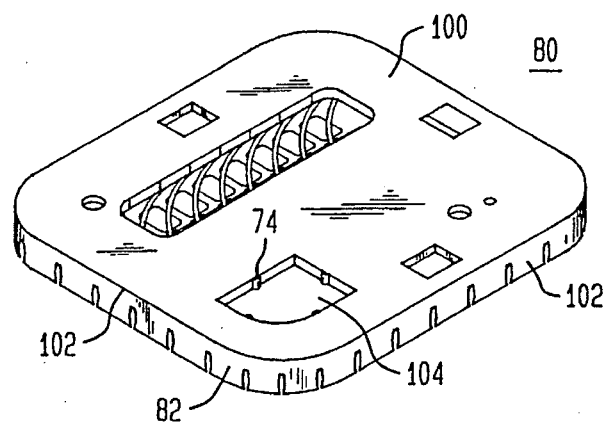
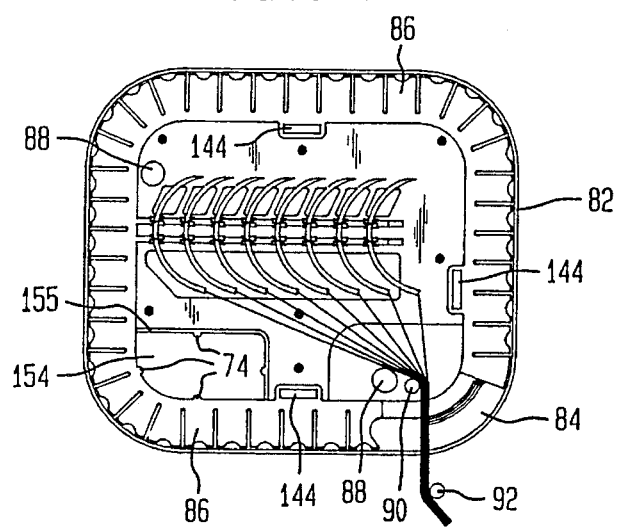
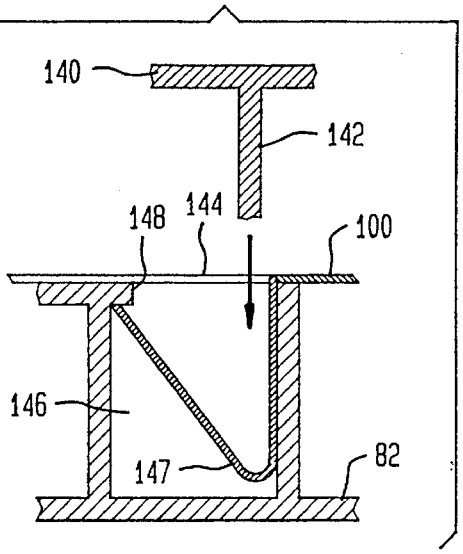

SUTURE WINDER MACHINE

BACKGROUND OF THE INVENTION

1. Field of the Invention

The present invention relates to a suture winder machine and, more particularly, pertains to a semi-automated suture winding station of the machine adapted to facilitate the high-speed winding of multiple sutures, which are each attached to needles, into a peripheral channel of a tray utilized for packaging the needles and attached sutures. Moreover, the invention is directed to the provision of an apparatus for the attachment of a cover to the tray containing the needles and attached sutures. The cover-attaching apparatus includes a novel structure to enable the separation of a product-identifying label as a component of the tray which will remain with the tray subsequent to the removal of the tray cover.

The packaging into suitable containments of either single or multiple sutures which are attached, such as by being swaged, to needles, whereby the attached needles and sutures are generally referred to as armed sutures, in order to meet the requirements of users of such combined surgical needles and sutures; for instance, such as surgeons or other health professionals, is well known in the health-related technology, and numerous and widely diverse types of inexpensively manufactured suture packages have been developed in industry.

In some instances, suture packages are designed to contain a multiplicity of needles and thereto attached sutures, whereby the suture packages must facilitate the uncomplicated withdrawal of individual needles and their attached sutures from the package in a smoothly implementable and unobstructed manner. In essence, when the needle is gripped; for instance, by means of a forceps, and pulled out of the suture package, it is necessary that the needle easily disengage from the package, while the suture which is attached to the withdrawn needle should also readily slide out of the package in the absence of any binding or snagging, and also without becoming entangled with other sutures still remaining in the suture package. Hereby, in a specific package construction, the needles are generally engaged by clamping structure so as to be "parked" or retained in a central region of a suture package, such as a flat tray, which may be formed from an injection-molded plastic material, wherein the sutures extending from the needles to which they are attached are conducted into and deposited in a peripheral channel formed about the suture tray and so as to extend within the peripheral confines thereof. This positioning of the needles, and particularly of the sutures, in the package or tray is intended to eliminate tight bends or curves normally imposed on the sutures and to reduce package shape memory associated therewith. The package shape also facilitates their easy individual withdrawal from the suture package without entanglement with the remaining sutures or snagging on the package.

A flat tray-shaped suture package has been presently developed in order to provide for the storage of multiple needles and sutures, and which takes cognizance of the need to facilitate the smooth and unhindered withdrawal of individual needles and therewith attached sutures from the suture package, as in a copending U.S. patent application entitled "Multi-Strand Suture Package and Cover-Latching", commonly assigned to the assignee of the present application; (identified under Attorney Docket ETH-849); and referred to as an RSO package (Reduced Size Organizer). In that particular constructional design, the suture package is basically a rectangular, round-cornered and flat-bottomed injection-molded plastic tray-shaped structure having a flat central surface area including a raised needle clamping structure formed thereon for engaging and "parking" a plurality of needles in a predetermined spaced array. Sutures each have ends attached to each of the respective needles so as to form so-called "armed sutures". The sutures extend from each of the needles into a channel extending about the perimeter of the suture tray and are conducted into the channel so as to be essentially wound within the peripheral confines of the suture package or tray.

The plurality of sutures which are located within the suture tray channel are basically protected against inadvertent outward dislocation through the presence of a multiplicity of contiguously positioned resilient fingers which are integrally formed with the suture tray, and which project outwardly over the confines of the channel along a major portion of the peripheral length of the channel and form collectively a so-called "zipper" structure in which the resilient nature of the fingers facilitates their temporary raising to enable the introduction of the sutures into the suture tray channel by means of suitable suture winding procedures.

2. Discussion of the Prior Art

Currently, the winding of the sutures into the suture tray channel is ordinarily implemented in that the suture package or tray containing the needles and attached sutures is manually rotated on a fixture to enable a device to temporarily deflect the resilient fingers upwardly in a successive order to thereby enable insertion of the sutures beneath the raised resilient fingers for depositing in the channel during rotation of the suture tray.

The foregoing substantially manual and relatively crude procedure for winding the sutures into the tray channel during rotation of the suture tray is quite time-consuming whereby, to a significant extent, it represents an obstacle to a high output rate and economical manufacture of mass-produced quantities of suture packages containing multiple needle and attached suture components.

SUMMARY OF THE INVENTION

Accordingly, in order to considerably improve upon the speed and quality in the winding of sutures during their loading into suture packages or trays, and especially sutures which are attached to needles to thereby constitute so-called armed sutures; particularly with regard to suture packages containing multiple needles and attached sutures, the present invention contemplates the provision of a suture winder station having a semi-automated winding machine wherein a substantially flat suture tray loaded with multiple needles and sutures extending therefrom is mounted on a rotatable platform incorporating registration structure for ensuring the appropriate mounting and positioning of the suture tray thereon. The winding machine structure is adapted to rotate the suture tray about an axis perpendicular to the planar surface thereof so as to enable the extending multiple sutures to be bundled and wound for depositing in a channel formed along the periphery of the suture tray. The winding machine includes cam-controlled stylus and suture guide structure with a following roller, with the stylus engaging successive resilient fingers on the tray which normally cover the channel. During rotation of the tray the suture guide guides the sutures into the channel beneath the raised fingers, whereby upon the stylus passing the raised resilient fingers, the following roller will return the raised fingers to their initial suture-protective position over the channel.

The winding machine also incorporates a vertically movable and rotatable platen structure which presses against the upper surface of the suture tray during rotational movement of the platform to ensure the maintaining of the continued flat positioning of the tray and of the needles in their "parked" positions within the tray while the extending multiple suture stands attached to the needles are being bundled, wound and deposited into the peripheral channel of the suture tray.

The suture winding machine is actuated by a suitable driving arrangement for controllably and automatically rotating the suture tray-mounting platform a sufficient number of revolutions to ensure that the sutures are fully wound and deposited in the peripheral channel of the suture tray within a minimum period of time, thereby extensively increasing the rate of production in the manufacture of the multiple suture and needle-loaded packages.

In addition to the foregoing, the application of a cover to the needle and suture-containing trays is implemented in a suitable inventive press having a jig which includes a platform having the tray mountable thereon, the cover being manually superimposed on a tray, and a die for pressing the cover into latching engagement with the tray so as to, while forming suitable interengaging latching locations, also separate a portion of the cover and press the separated portion into the tray for permanent attachment thereto upon removal of the cover. This attached separated portion of the cover remaining connected to the tray forms a product-identifying label.

Moreover, the provision of the cover-attaching apparatus pursuant to the invention also ensures that, subsequent to the completion of the winding of the sutures at the winding station, covers can be applied to the tray and subjected to pressure which will form latching members in the cover engaging with complementary latching elements on the tray, and concurrently separate a portion of the cover and fixedly position the separated portion in a suitable recess formed in the tray so as to provide a permanent separate label which, as required, may possess various products identifying information and suitable indicia, as mentioned hereinabove.

Accordingly, it is a primary object of the present invention to provide a suture winder station having a semi-automated winding machine for winding bundled multiple sutures which are each respectively attached to a needle into a peripheral channel formed in a suture tray.

Another object of the present invention is to provide a winding machine for the semi-automated winding of multiple sutures each connected to needles into a peripheral channel formed in a generally flat tray-shaped suture structure at high rates of winding speeds.

Still another object of the present invention is to provide a suture winding machine of the type described, wherein the tray-shaped suture package containing a plurality of needles each having attached sutures extending therefrom is supported for rotation on a rotatable platform of the winding machine, and is revolved about an axis perpendicular to the plane of the tray to ensure the complete depositing of the full lengths of the sutures into a peripheral channel of the suture tray.

A further object of the present invention is to provide a semi-automated winding station for the winding of armed sutures as described, wherein the winding machine is equipped with a cam-controlled stylus and suture guide such that, during rotation of the platform supporting the suture tray, successively raised resilient fingers of the suture tray which extend over the suture-receiving peripheral channel enable the continual depositing of the sutures into the channel of the suture tray.

A still further object of the present invention is to provide a cover-attaching apparatus which will enable the positioning of a cover on the needle and suture-containing tray into which the sutures have been previously wound, and the application of a pressure die imparting a suitable pressing action against the cover which will produce latching structure thereon cooperatively engaging with latching elements on the tray, and concurrently separate a surface portion of the cover to form a label permanently fastened to the tray subsequent to the removal of the cover therefrom.

BRIEF DESCRIPTION OF THE DRAWINGS

Reference may now be had to the following detailed description of a preferred embodiment of a winder machine incorporating a semi-automated winding station for winding sutures in a tray-shaped suture package, taken in conjunction with the accompanying drawings; wherein:

FIG. 7 illustrates a perspective view of a complete covered tray-shaped suture package in which the sutures have been wound by the semi-automated suture winding station pursuant to the invention;

FIG. 8 illustrates a top plan view of the suture tray prior to suture winding, or the placement of the cover;

FIG. 10 illustrates, on an enlarged scale, a fragmentary cross-sectional view of a cover tab formed in the cover for the suture tray pursuant to FIG. 8, held in a cover-latching element of the tray and the insertion tool for inserting the tab;

DETAILED DESCRIPTION OF A PREFERRED EMBODIMENT

Figure 1:
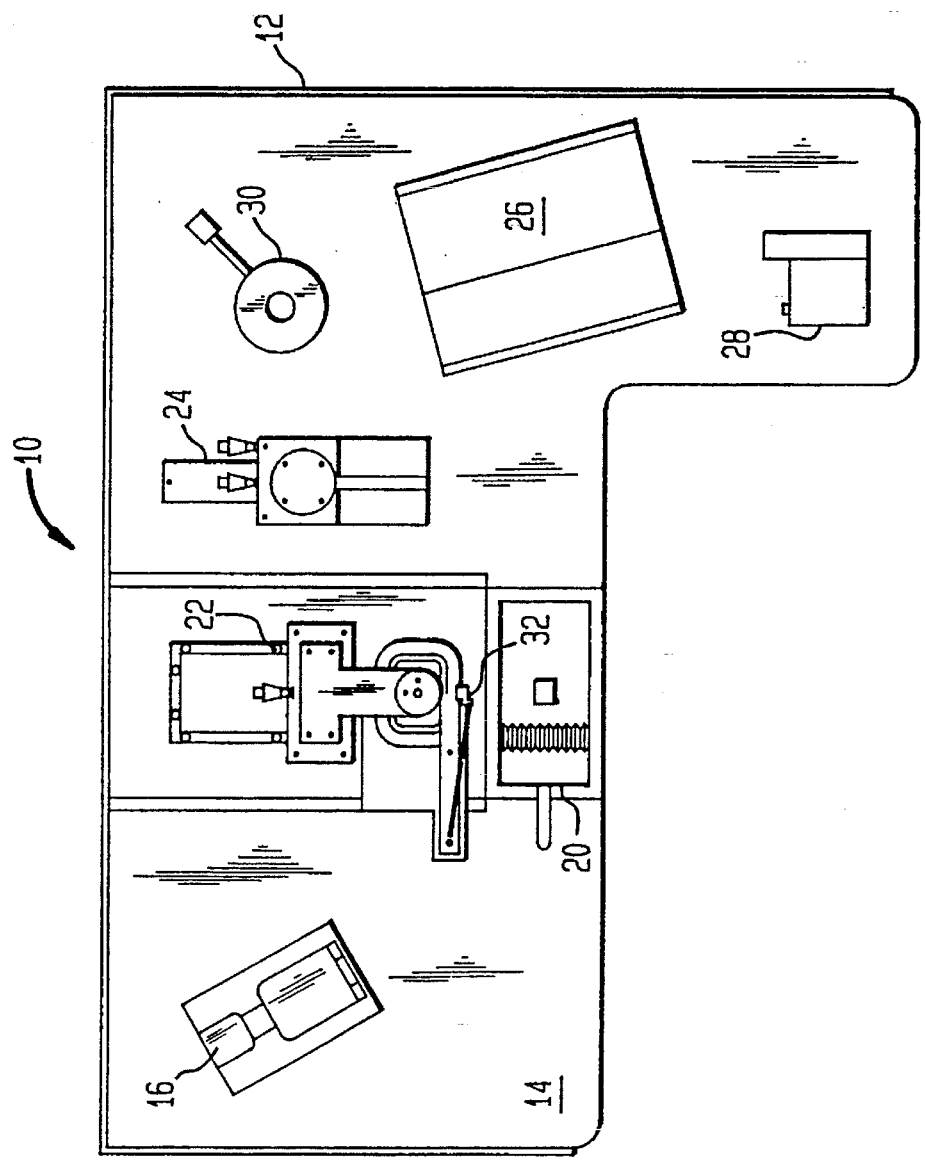
FIG. 1 illustrates a top plan view of the table diagrammatically illustrating the positioning of the various operative components including the semi-automated suture winding machine constructed pursuant to the invention.

Referring now in more specific detail to the drawings, and particularly to FIG. 1, there is disclosed a suture winder work station 10 which includes a winder table 12 possessing a work surface 14 for supporting thereon the various operative components employed in the winding of armed sutures into suture trays and formulating complete suture packages. In particular, work station 10 is essentially considered to be a semi-automatic work station, inasmuch as the loading of the trays with needles and attached sutures, and conveying and positioning the trays in the semi-automated winding machine 22 is carried out manually, and it is primarily the suture winding sequence which is implemented in an automatic mode. The subsequent attachment of covers to the suture trays is also semi-automatic with conveying and positioning of the trays in the label station and the positioning of the label being carried out manually and with the label application implemented in an automatic mode.

As shown in the generally schematic representation of FIG. 1, the suture winder station 10 includes a plurality of discrete operating components which are mounted or positioned on the working surface 14 of the winder table 12, and which may include a dispenser unit 16 consisting essentially of a dispensing chute having a vertical stack of RSO (Reduced Size Organizer) suture trays contained therein. The suture trays, as described in more extensive detail with regard to FIGS. 8, 9 and 10 of the drawings, are basically flat-bottomed tray members preferably constituted of an injection-molded plastic material and are adapted to be dispensed singly from the dispenser unit 16 so as to enable manual (or possibly mechanized) loading of the dispenser trays with needles and attached sutures.

In order to implement this tray loading process, located on the work surface 14 so as to be accessible to an operator may be a needle park station 20 which includes a support for empty suture trays received from the dispenser unit and cooperating movable structure mounting a plurality of needles which are adapted to be swung into the tray so as to be clampingly engaged therein and resultingly "parked" at predetermined locations, with such needles previously having been attached to sutures which loosely extend from the tray.

Figure 3:
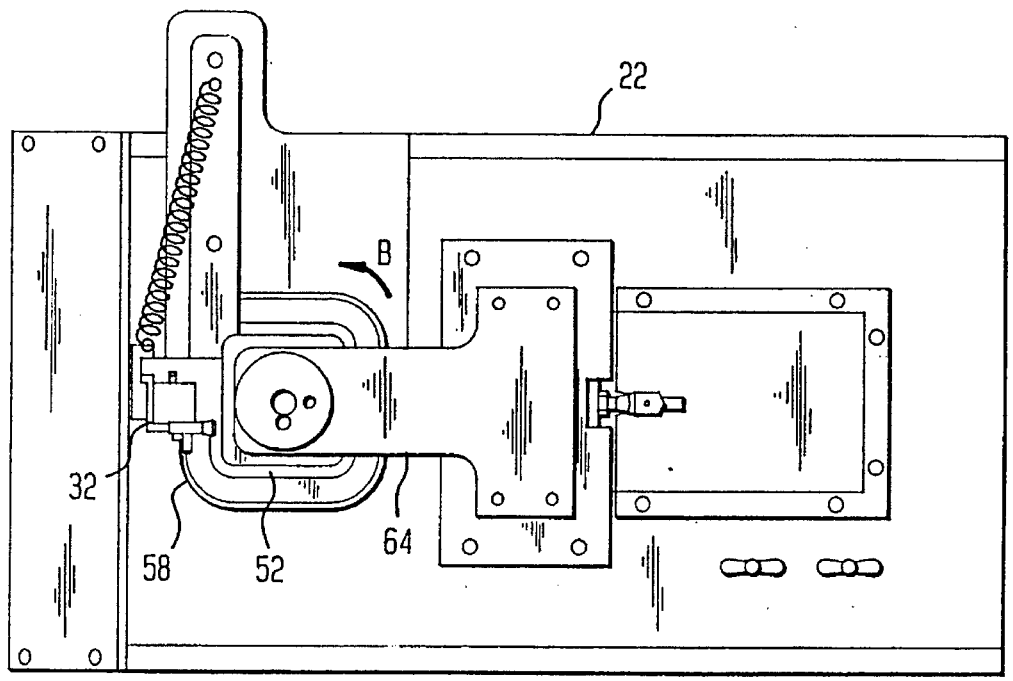
FIG. 3 illustrates a top plan view of the winding machine, taken in the direction of arrow A in FIG. 2.
Figure 2:
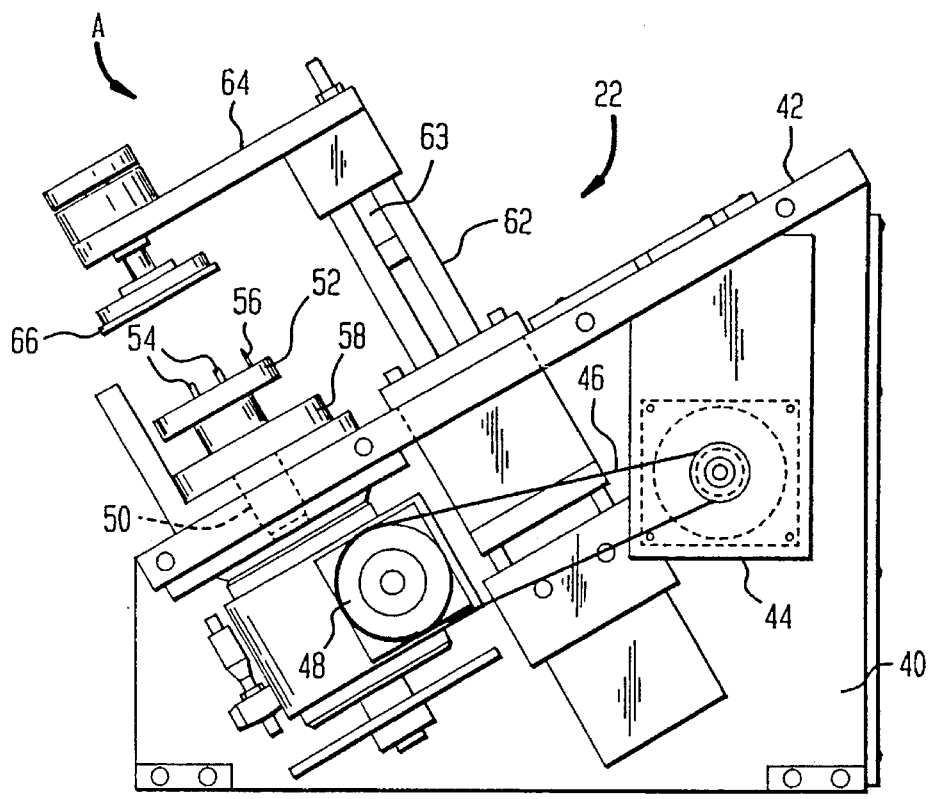
FIG. 2 illustrates, on an enlarged scale, a side elevational view of the semi-automated suture winding machine which is arranged on the table of FIG. 1.

A semi-automated winding machine 22, as illustrated in more specific detail in FIGS. 2 and 3 of the drawings, is adapted to automatically bundle and then wind the lengths of the sutures extending from the needles mounted in the suture tray into a peripheral channel formed in the tray.

Subsequent to the sutures having been wound into the suture tray at the semi-automated winding machine 22, the tray with the wound sutures contained therein are then adapted to be manually transferred to a suitable pressing station 24 in which a cover is adapted to be applied to the tray and fastened thereto through the application of pressure to the cover, as explained in further detail hereinbelow.

A suitable tote box holder unit 26 is also positioned on the work surface 14, and a demagnetizer assembly 28 adapted to demagnetize any packaged needles subsequent to the completion of the cover-attaching pressing sequence at station 24. A task light 30 is adapted to be mounted on the surface 14 of the winder table 12.

Figure 4:
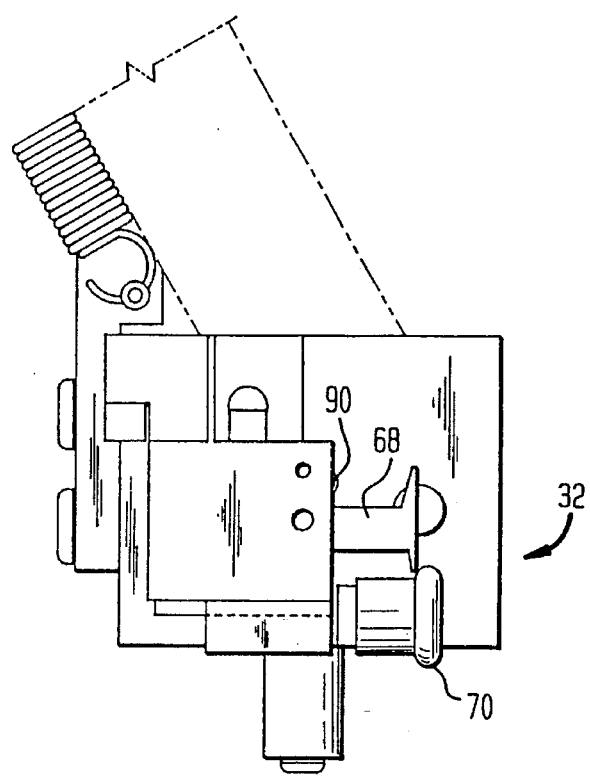
FIG. 4 illustrates a top plan view of a stylus and suture guide unit of the winding machine.
Figure 5:
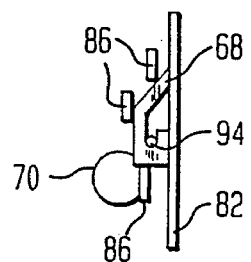
FIG. 5 illustrates a side view of a portion of the stylus and suture guide unit illustrated in FIG. 4.
Figure 6:
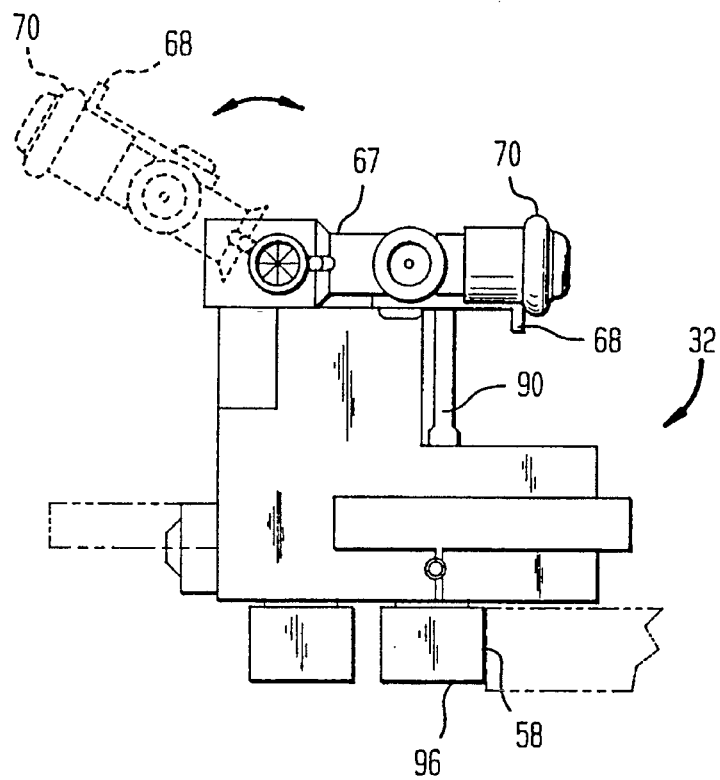
FIG. 6 illustrates a side view of the assembly of FIG. 4.

Arranged at the winding machine 22 is a cam-controlled stylus and suture guide unit 32 employed in connection with the automated winding of the sutures, as described in further detail with regard to FIGS. 4, 5 and 6 of the drawings.

The semi-automated suture winding machine 22 pursuant to the invention, as shown in detail in FIGS. 2 and 3 of the drawings, includes a housing 40 which is supported on the work surface 14 of the winder table 12; the upper end of which housing has an inclined plate member 42 thereon below which there is located a drive arrangement for the winding machine 22. The arrangement includes a drive stepper-motor 44 which is connected through the intermediary of a drive belt 46 with a suitable pulley 48 which, in turn, is operatively connected with a rotatable shaft arrangement 50 extending upwardly through the inclined plate 42 perpendicular thereto.

Fastened to the upper end portion of the shaft 50 is a platform 52, the surface of which has generally the configuration of the flat suture tray, and which incorporates spaced upstanding pin members 54 and also a registration pin 56, which are adapted to engage into apertures formed in the bottom wall of the suture tray, as discussed in further detail hereinbelow, so as to mount the tray in a specified orientation on the platform 52.

Mounted on the shaft 50 below the platform 52 is a cam plate 58 for rotation in conjunction therewith, and wherein the cam plate has an outer peripheral surface 60 forming a camming surface of a shape substantially in conformance with the outer peripheral shape of a suture-receiving channel in the suture tray.

Extending in parallel spaced relationship with the longitudinal axis of shaft 50 and supported on the plate 42, is a vertical column 62, which may have a pneumatically or hydraulically actuatable, axially movable piston member 63 arranged therein, at the upper end of which there is fastened a cantilevered beam 64. A rotatable platen 66 is suspended below the beam 64 in coaxial alignment with the longitudinal axis of the platform 52. The platen 66 has a configuration substantially in correlation with the center portion of the tray inwardly of the inner periphery of the channel in the tray.

The stylus and guide unit 32 is positioned so as to be oscillatable on the winding station 20 adjacent the platform 52, as is shown in FIG. 3 of the drawings and; as illustrated in greater detail in FIGS. 4, 5, 6 and 9, in which FIG. 4 is a top view, FIG. 5 is a sideview and FIG. 6 is an elevational view, and includes a pivotable frame 67, with a stylus 68 being located adjacent a finger closing back down roller 70, both of which components 68, 70 being adapted to be pivoted about a shaft 72. The unit 32 is operatively biased against cam surface 58 which is rotated by the drive arrangement 48. In operation, the suture guide unit is used in synchronism with the axial movement of the piston in the column 62 and the rotation of shaft 50 for guiding the suture strands into a tray 82 positioned on platform 52.

The suture package 80, as shown in FIG. 7 of the drawings, is described in specific detail in the above-mentioned copending U.S. patent application entitled "Multi-Strand Suture Package and Cover-Latching Element" (Attorney Docket ETH-849), the disclosure of which is incorporated herein by reference.

OPERATION OF THE SEMI-AUTOMATED WINDING STATION

As illustrated in FIG. 1, preceding the activation of the winding station 22, as mentioned hereinbefore, the tray-shaped portion 82 of the suture package 80, as described in the copending patent application, is removed from the stack of trays in dispenser unit 16, and a specified quantity of needles, each with an attached suture, are inserted therein by means of a needle jig 20, so as to be clampingly engaged in their "parked" arrayed positions in the central region of the tray 82. The needles may be inserted manually, semi-automatically or automatically to form the needle and suture package illustrated in FIG. 8.

The sutures which are attached to each of the needles, initially extend loosely outwardly of the tray 82, as illustrated in FIG. 8, and are manually aligned above a space 84 formed between a series of adjacently located resilient fingers 86 which extend over a channel 87 formed in the tray 82, wherein the channel 87 extends about the periphery of the suture tray 82.

In order to implement the automatic winding of the sutures into the channel 87 of the suture tray 82, the tray is positioned on the platform 52 such that the pins 54 project through apertures 88 formed in the tray, and with the third registration pin 56 extending through a further aperture 90 in the tray so as to ensure the tray 82 is positioned in a predetermined orientation relative to the platform 52 and the stylus and suture guide unit 32.

Thereafter, the loosely extending strands of the sutures are bunched and placed about the registration pin 56, while the roller is in its pivoted open position about shaft 72 as represented by the phantom line in FIG. 6. In order to place the sutures which loosely extend from the tray into a bunched condition, the sutures are manually gripped and guided about the third registration pin 56, which acts as a guide element, and then manually guided about a capstan 92 (shown in FIG. 6 and diagrammatically in FIGS. 6 and 9) located externally of the winding station. Thereafter the combined stylus 68 and guide roller 70 are pivoted downwardly and forwardly about the pivot shaft 72 so as to cause the bunched sutures to be placed above channel 87 of the tray 82 and into a suture guide 94 of suture guide shoe 68. The sutures may then released from their manual engagement to permit activation of the winding station 22, or may be loosely held while being wound into the tray.

Figure 9:
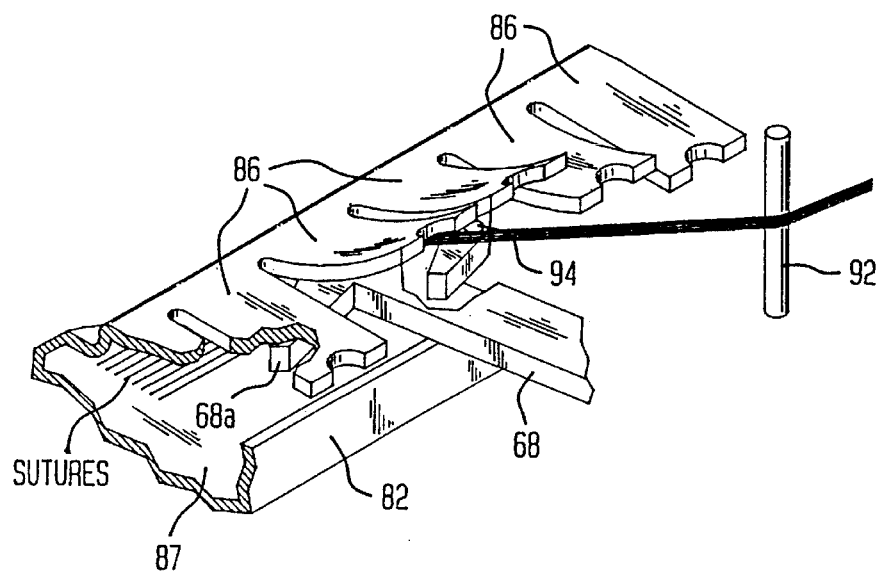
FIG. 9 illustrates, on an enlarged scale, a fragmentary sectional view showing the insertion and positioning of the sutures in the peripheral channel of the suture tray of FIG. 8.

The winding station 22 is then activated, in that the cantilevered arm 64 with the platen 66 thereon is moved downwardly by the driving arrangement until the lower surface of the platen contacts the central portion of the suture tray 82 which is mounted on the platform 52 so as to ensure that the needles are maintained in their parked flat position, and the tray locked down on the platform so as to maintain engagement with the pins 54 and 56. The platform 52 is then set into rotation about its central axis in the direction of arrow B (in FIG. 9), and the outer peripheral configuration of the cam 58, essentially correlated to the shape of the tray 82 mounted on the platform 52, is contacted by a cam follower 96 on the stylus and suture guide unit 32, such that during oscillatory movement of the latter, the stylus 68 will successively raise the resilient fingers 86 on the suture tray as illustrated in FIGS. 5 and 9 and the guide 94 of stylus 68 will cause the sutures to be continually deposited along their lengths in the peripheral channel 87 of the suture tray 82, as shown in FIG. 9 of the drawings. Guide roller 70 ensures that each of the resilient fingers is turned to its original orientation.

Upon a specific number of revolutions having been implemented by the platform 52 and the tray 82 thereon, in accordance with the length of the sutures which are to be wound into the channel of the suture package, as determined by a suitable control system (not shown), the winding station 22 will cease operation setting the platform 52 at rest. The control system also tracks the rotation of stepper motor 44 to ensure that the rotation of the tray begins and ends with the stylus positioned in the open portion 84 of track 87 to enable the positioning and removal of stylus 68. The control system then causes the piston in column 62 to move upwardly so as to disengage the platen 66 from the suture tray, and causing the stylus 68 and back roller 70 to be pivoted into their initial inoperative positions. This will enable the operator of the machine to manually remove the suture tray 52 with the wound sutures therein from the winding station 22, and to position the tray at the cover-applying station 24 so as to enable completing the covering and packaging of the needles and attached wound sutures contained in the tray 82, as set forth hereinbelow.

Figure 12:
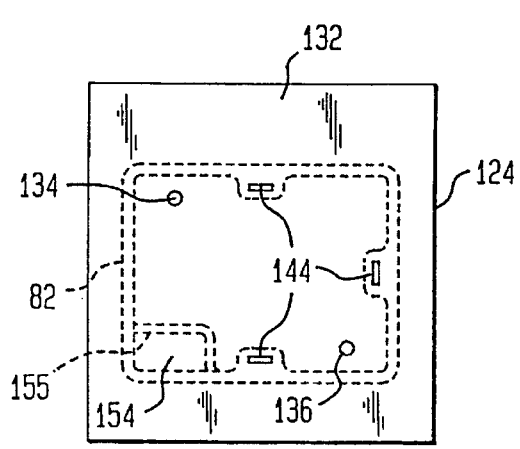
FIG. 12 illustrates, on an enlarged scale, a view taken in the direction of arrow 12—12 in FIG. 11.
Figure 13:
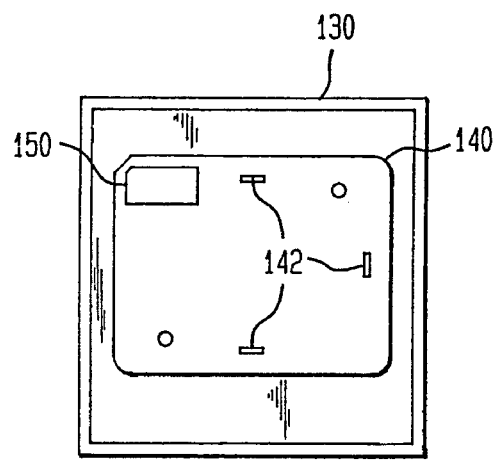
FIG. 13 illustrates, on an enlarged scale, a view taken in the direction of arrow 13—13 in FIG. 11.
Figure 11:
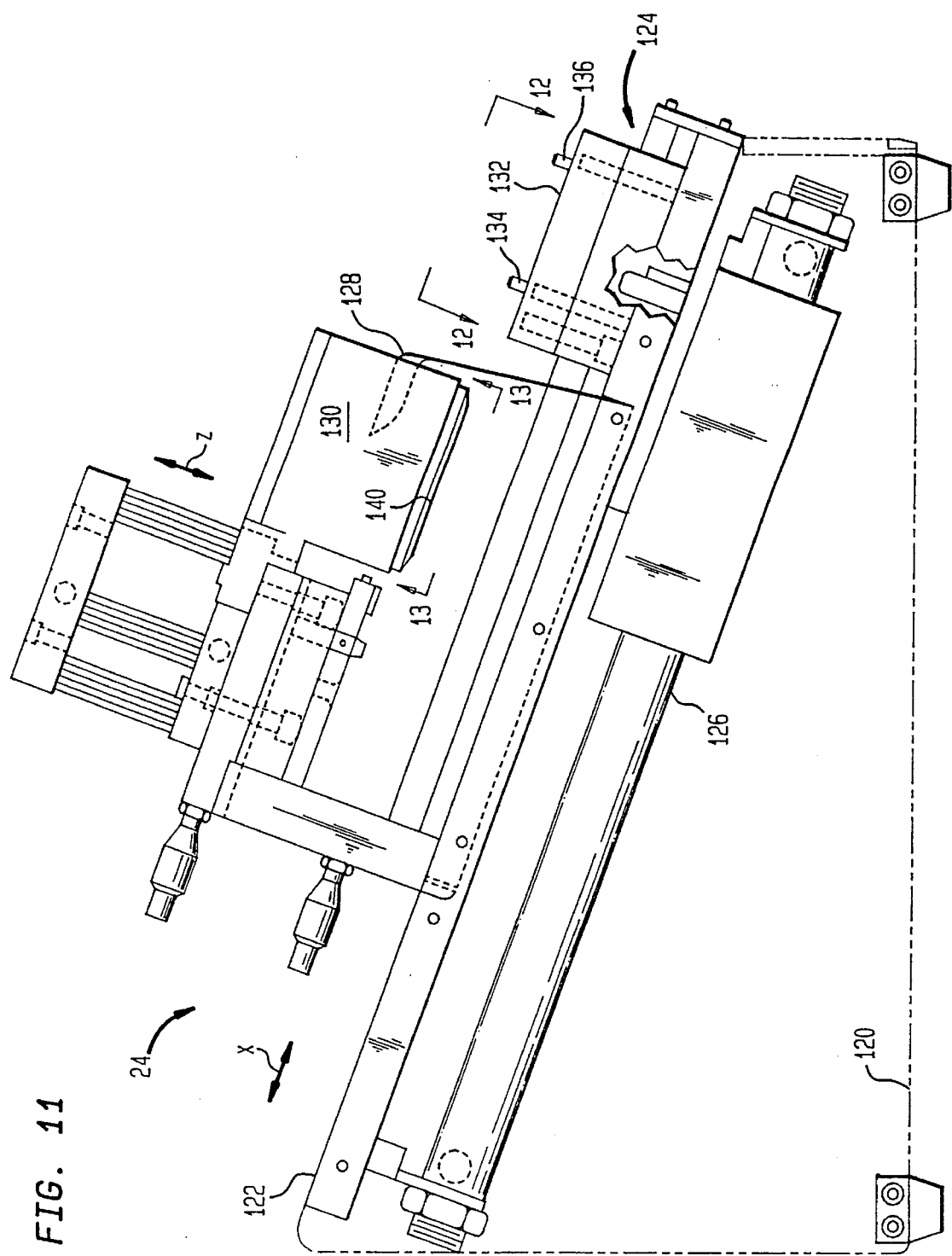
FIG. 11 illustrates a generally diagrammatic side elevational view of a cover-attaching apparatus for fastening the cover to the tray.

Reverting now in more specific detail to the cover-applying or attaching station 24, as shown in FIGS. 11, 12 and 13 of the drawings, the station 24 includes a supporting frame or stand 120 which is positioned on the surface 14 of the work table 12 adjacent to the winding station 22, as shown, for example, in FIG. 1 of the drawings. The upper surface of the stand 120 includes an inclined plate 122 having a longitudinal slide formed therein to enable the movement of a lower tray receiving jig 124 along the incline in the direction of arrow X. This movement in the direction of the arrow X is afforded by the attachment of the tray receiving jig 124 to a suitable cylinder and drive unit 126, also displaceable through suitable hydraulic or pneumatic actuation along the direction of the arrow X.

Fastened to an upper stand or frame structure 128 is an upper position 130 which may be moved downwardly and upwardly in a reciprocatory motion along arrow Z, perpendicular to the direction of movement of lower pressure die 124 along its axis X.

The upper surface 132 of the tray receiving jig 124 is illustrated in FIG. 12 Of the drawings, with the walls of tray 82 illustrated in dotted lines. This upper surface 132 is flat and includes a pair of upstanding pins 134 and 136, which are correlated with the openings 88 in the tray 82, when the latter is positioned thereon.

The operation of the cover-applying or attaching station 24 is essentially as follows:

Subsequent to the completion of the winding process of the sutures into the channel 87 of the tray 82 on the winding station 22, the tray 82 with its contents is manually removed therefrom and then positioned on the surface 132 of the tray receiving jig 124 so that the pins 134 and 136 extend through the openings 88, thereby orienting the tray 82 on the surface 132. Thereafter, a flat cover 100, which may be of a suitably imprinted paperboard or the like material, is applied over the tray 82, as shown in FIG. 7, with the outer dimensions of the cover being substantially coextensive with the peripheral dimensions of the tray 82, and with the cover also having apertures 88 in registration with the upstanding pins 134 and 136 on the surface 132, analogous to registration pin 56 at the winding station 22.

Thereafter, the unit 126 is actuated causing the tray receiving jig 124 to be displaced upwardly along the inclined plate 122 along the direction of arrow X until positioned directly in alignment below the downwardly facing surface of the upper piston 130.

The lower surface of the upper piston includes a first die 130 illustrated in FIG. 13 and with a surface portion 140 substantially in conformance with the flat surface of the cover 100 which has been superimposed on the tray 82, and includes three protruding dies 142, preferably at three sides about the surface 140, one of which is shown in enlarged scale in FIG. 10 of the drawings, which enter slots 144 above the recessed portions 146 of the tray, and cause the cover 100 to be folded within the recess 146 to form latching tabs 147 so as to have the edge of the formed tab 147 at that location engage beneath a horizontal wall structure 148 of the tray 82 extending partially over the recess 146, thereby latching the cover 100 into cooperative engagement with the upper surface of the tray.

Concurrently, a second and raised die portion 150 on the surface 140 of the upper die 130 engages into a surface region 154 defined by suitable raised wall structure 155 on the tray 82. During the manufacturing process, cover 100 is manufactured such that a defined portion 104 is cut along its perimeter with the exception of several uncut tie points which serve to keep it integral with cover 100. Second die means 150 and wall 155 form therealong a peripheral punch commensurate with the perimeter of surface 154 so as to break away the defined portion 104 of the cover 100 in conformance with the surface region 154, and die 150 pushes the severed cover portion 104 downwardly into that area 154 of the tray so as to be separate therein severed from the remaining structure of cover 100. The separate portion is retained within tray 82 by one of more ribs 74, illustrated in FIGS. 7 and 8 which are formed in wall 55.

Thereafter, the upper pressure die 130 is again raised, also through automated hydraulic or pneumatic actuation, the lower die 124 concurrently displaced downwardly along the inclined surface 122 by means of the operating unit 126, and the completed covered suture package 80 may then be manually removed for further processing, as desired.

In summation, the applied cover 100 is essentially separated into two portions, of which the first portion 102 is applied to a first planar area over the tray 82 and the second one of the cover portions 104 is severed therefrom, recessed and affixed to the recessed planar area 154 within the tray 82. Consequently, upon removal or peeling off of the first portion 102 of the cover 100 from the package 80, access is provided from the exterior to the needles so as to enable sequential withdrawal thereof, including the sutures which are attached thereto, whereas the second separated portion 104 of the cover 100 which is affixed in the recessed part 154 of the tray remains therein and may render visible therein suitable identifying legends concerning the size and type of needle and suture in the tray.

From the foregoing description, it becomes clearly evident that the winding station 22 enables the automated winding of sutures in a rapid and expedient manner which will obviate the necessity for manual winding of such sutures, thereby providing a cost-effective mode of accelerating the production of suture packages containing a plurality of needles and attached sutures.

Moreover, the cover-applying station 24 also facilitates the rapid and substantially automated application of a cover 100 to the tray 82 having the needles parked therein and the attached sutures wound into the channel of the tray, thereby enabling the rapid production of needle and suture packages 80 with a minimum degree of manual handling and manipulation.

Furthermore, although the foregoing arrangement has been described in connection with the winding of a plurality of strands of sutures, it becomes readily apparent to one of skill in the art, that a single suture may also be readily wound in a tray-shaped suture package and; moreover, rather than employing the illustrated rectangular suture package, the package may have other suitable peripheral configurations; for example, such as ovoid, circular or the like.

While there has been shown and described what is considered to be a preferred embodiment of the invention, it will of course be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. In a winder machine for sutures including a semi-automated winding station for receiving a tray having a plurality of needles and attached sutures mounted therein, wherein said winding station automatically winds the plurality of sutures extending from said needles into a peripheral channel of said tray; said winding station comprising:

(a) rotatable tray holder means; means for retaining said tray on said holder means including at least one registration means for positioning said tray at a predetermined orientation relative to said holder means;

(b) cam means fastened to said tray holder means and having a camming surface in conformance with the configuration of the peripheral channel of said tray;

(c) drive means for conjointly imparting rotation to said tray holder means and cam means;

(d) and winding structure arranged adjacent said tray holder means and operatively connected with said cam means for gathering the extending sutures into a single bundle and guiding said sutures into said channel during revolving of said holder means.

2. A semi-automated winding station as claimed in claim 1, wherein said winding structure includes a suture guide for guiding said bundled sutures into said tray channel.

3. A semi-automated winding station as claimed in claim 2, wherein said tray includes a plurality of resilient cantilevered fingers extending over said peripheral channel for protectively maintaining the sutures in said channel, said suture guide further comprises a stylus member engaging beneath successive ones of said fingers for raising said fingers during rotation of said tray holder means to enable said suture guide to sequentially raise said fingers to insert said bundle of sutures into said tray channel.

4. A semi-automated winding station as claimed in claim 3, wherein said stylus member and suture guide further include a roller for sequentially closing said fingers following said stylus.

5. A semi-automated winding station as claimed in claim 4, wherein said winding structure includes a cam follower contacting the camming surface of said cam means so as to enable the stylus member and suture guide to follow the contour of said tray channel in the operative condition thereof.

6. A semi-automated winding station as claimed in claim 1, wherein said tray holder means includes a platform for supporting said tray, and a plurality of said registration means for simultaneously orienting and securing said tray to said platform.

7. A semi-automated winding station as claimed in claim 6, wherein said registration means comprise upstanding pins fastened to said platform and being engageable in apertures formed in said tray.

8. A semi-automated winding station as claimed in claim 7, wherein at least one said pin comprises a reference point for gathering said sutures into a bundle.

9. A semi-automated winding station as claimed in claim 1, wherein an axially displaceable and rotatable platen is movable into contact with said tray for maintaining said tray in engagement with said tray holder means during rotation thereof while winding the bundle of sutures into the peripheral channel of said tray.

10. A semi-automated winding station as claimed in claim 9, wherein said platen is axially displaced towards said tray responsive to hydraulic actuation thereof.

11. A semi-automated winding station as claimed in claim 6, wherein said drive means rotates said tray and platform a specified number of revolutions to ensure the entire extending lengths of said sutures are wound into the tray channel.

12. A semi-automated winding station as claimed in claim 1, comprising a cover-applying station for applying a cover to said tray after said sutures have been wound into said channel of the tray.

13. A semi-automated winding station as claimed in claim 12, wherein said tray includes first and second planar areas, said cover-applying station includes pressure-imparting means for separating said applied cover into two portions, a first of said portions being applied to said first planar area and a second of said portions being affixed to said second planar area.

14. A semi-automated winding station as claimed in claim 13, wherein said pressure-imparting means includes means for forming tabs in said cover for latching engaging cooperating latching elements on said tray during the application of said cover thereto.

15. A semi-automated winding station as claimed in claim 14, wherein said pressure-imparting means is pneumatically actuated.

* * * * *